United States Patent [19]
Roos et al.

[11] 3,931,231
[45] Jan. 6, 1976

[54] 4,5,6,7-TETRACHLORO-2-THIO-PHTHALIDE

[75] Inventors: Ernst Roos, Odenthal-Osenau; Klaus Wagner, Cologne; Hans Scheinpflug, Leverkusen, all of Germany

[73] Assignee: Bayer Aktiengesellschaft, Leverkusen, Germany

[22] Filed: Oct. 31, 1974

[21] Appl. No.: 519,716

[30] Foreign Application Priority Data
Dec. 11, 1973  Germany.......................... 2361513

[52] U.S. Cl....... 260/330.5; 260/502.6; 260/544 M; 424/275
[51] Int. Cl.²..................................... C07D 333/72
[58] Field of Search............................... 260/330.5

[56] References Cited
OTHER PUBLICATIONS
Chemical Abstracts 66:2430s (1967) Yagupolskii et al.

*Primary Examiner*—Sherman D. Winters
*Attorney, Agent, or Firm*—Burgess, Dinklage & Sprung

[57] ABSTRACT

4,5,6,7-Tetrachloro-2-thio-phthalide of the formula

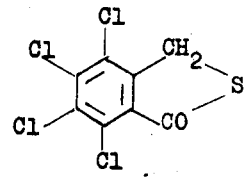

which possesses fungicidal and bactericidal properties.

8 Claims, No Drawings

4,5,6,7-TETRACHLORO-2-THIO-PHTHALIDE

The present invention relates to and has for its objects the provision of the new compound 4,5,6,7-tetrachloro-2-thio-phthalide, which possesses fungicidal and bactericidal properties, active compositions in the form of mixtures of such compound with solid and liquid dispersible carrier vehicles, and a method for producing such compound and for using such compound in a new way especially for combating pests, e.g. fungi and bacteria, with other and further objects becoming apparent from a study of the within specification and accompanying examples.

As evidenced by R. Wegler, "Chemie der Pflanzenschutz- und Schadlingsbekampfungsmittel" ("Chemistry of Plant Protection Agents and Pesticides"), Springer-Verlag, Heidelberg (1970) page 65, it has been generally known for a considerable time that the zinc salt of ethylene-bis-dithiocarbamic acid (Compound A) is suitable for combating plant diseases caused by fungi; the compound mentioned is a commercially available product used world-wide. Earlier, organo-mercury compounds were used extensively for specifically combating fungi which cause diseases in rice plants. While these compounds are of high fungicidal potency, they are dangerous for toxicological reasons.

The present invention provides, as a new compound, 4,5,6,7-tetrachloro-2-thio-phthalide, which has the formula

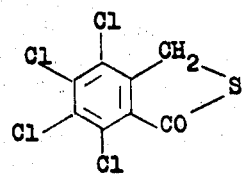

Surprisingly, 4,5,6,7-tetrachloro-2-thio-phthalide shows a greater fungicidal action than the generally known standard preparation zinc ethylene-bis-dithiocarbamate. The compound according to the invention thus represents an enrichment of the art.

The present invention also provides a process for the preparation of 4,5,6,7-tetrachloro-2-thio-phthalide, in which an alkali salt of 2-mercaptomethyl-3,4,5,6-tetrachloro-thiolbenzoic acid, of the general formula

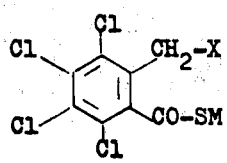

in which
X is SH or SM, and
M is an alkali metal,
is treated with an acid.

It is surprising that simple acidification of the alkali metal salt of the formula (II) gives the new compound (I) in a simple reaction and in good yield. This is unexpected, since it is known from A. W. Day and S. Gabriel, Berichte Vol. 23 (1890) page 2482 that sodium salts of 2-mercaptomethylbenzoic acid on acidification give the entirely stable 2-mercaptomethylbenzoic acid. However, the corresponding completely nuclear-chlorinated 2-mercaptomethyltetrachloro-benzoic acid proved incapable of isolation in the free form in numerous experiments both at low temperatures and with weak acids and in these experiments, surprisingly, tetrachlorothiophthalide was always obtained.

If the disodium salt of 2-mercaptomethyl-3,4,5,6-tetrachloro-thiolbenzoic acid is used for the preparation of the compound (I) and acidification is carried out with concentrated hydrochloric acid, the course of the reaction can be represented by the following equation:

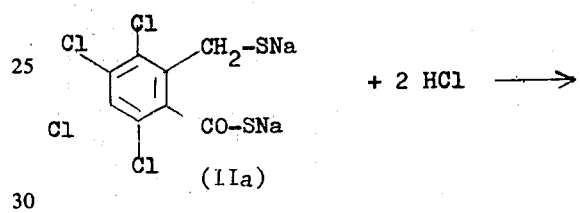

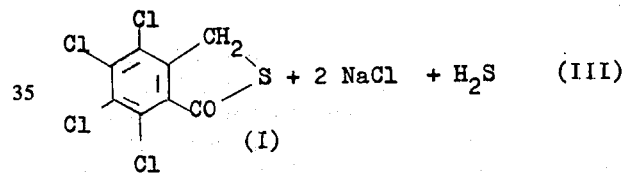

In formula (II), M is preferably sodium or potassium. Examples which may be mentioned are the disodium salt or dipotassium salt of 2-mercaptomethyl-3,4,5,6-tetrachlorothiolbenzoic acid; in this case, X in the formula (II) represents the radical —SM, i.e. -SNa or -SK. Further examples which should be mentioned are the monosodium salt or monopotassium salt of 2-mercaptomethyl-3,4,5,6-tetrachlorothiobenzoic acid; here, X in the formula (II) represents the radical —SH. The salts of the formula (II) are obtained by reacting 2-chloromethyl-3,4,5,6-tetrachlorobenzoyl chloride obtained by nuclear chlorination of o-toluic acid chloride and subsequent side-chain chlorination according to the instructions in U.S. Pat. No. 3,253,900, with, for example, the stoichiometric amount of sodium hydrogen sulfide in alcoholic solution, for example in methanol or ethanol. This reaction can be carried out in the temperature range between 0° and 100°C, preferably between 20° and 80°C.

Any desired organic or inorganic acids can be used for acidifying the alkali metal salts. For example, formic acid, acetic acid, hydrochloric acid, sulfuric acid and phosphoric acid are suitable. The cheap mineral acids such as hydrochloric acid and sulfuric acid are preferred.

As diluents it is possible to use water-miscible organic solvents; alcohols, such as methanol or ethanol, or ketones, such as acetone, are especially suitable for this purpose.

The acidification of the alkali metal salts can be carried out in the temperature range between about −10° and 40°C; preferably, temperatures between about 0° and 20°C are used.

In carrying out the process according to the invention, the equivalent amount of acid required for the reaction is generally employed per mole of dialkali metal salt or monoalkali metal salt of the general formula (II). An excess of acid is not necessary and it suffices, for the formation of the product, to reach a weakly acid pH range of about pH 5 to 6.

The working-up of the reaction mixture can be carried out by filtering off the compound (I) which precipitates after acidification, washing it with water and acetone and drying it.

Following the more extensive working up, the compound obtained is of satisfactory purity. If a fine purification of the product is of interest, the following procedure can be employed: the crude product is dissolved in aqueous alkali metal hydroxide solution and impurities are filtered off. The solution then contains a monoalkali metal salt or dialkali metal salt of 2-mercaptomethyl-3,4,5,6-tetrachloro-benzoic acid. These salts are then converted into the pure compound (I) on acidification.

According to an advantageous embodiment, the preparation of the compound (I) can be carried out by reacting 2-chloromethyl-3,4,5,6-tetrachloro-benzoyl chloride, in alcholic solution, with sodium hydrogen sulfide, keeping the resulting monosodium salt or disodium salt of the formula (II) in solution without isolating it, and adding the acid after cooling to the above-mentioned temperature range. The preparation of the compound (I) can in this way be carried out in a simple manner.

As mentioned at the outset, the compound according to the invention exhibits a strong fungitoxic action; it also exhibits a bacteriotoxic action. It does not damage crop plants in the concentrations required to combat fungi and has a low toxicity to warm-blooded animals. For these reasons it is suitable for use as a plant-protection agent for combating fungi and bacteria. Fungitoxic agents are employed in plant protection to combat *Archimycetes*, *Phycomycetes*, *Ascomycetes*, *Basidiomycetes* and *Fungi Imperfecti*.

The active compound according to the invention has a broad spectrum of action and can be employed against parasitory fungi and bacteria which attack above-ground parts of plants or attack the plants through the soil, and against seed-borne pathogens.

The active compound according to the invention has proved of particular value in combating diseases of rice. Thus it shows an excellent action against the fungi *Pyricularia oryzae* and *Pellicularia sasakii*, as a result of which it can be employed for conjointly combating these two fungi. This represents an advance since hitherto agents of different chemical structure have in most cases been required to combat these two fungi.

However, the compound according to the invention is also active against other fungi which attack rice plants or other crop plants, such as, for example *Cochliobolus myiabeanus*, *Mycosphaerella musicola*, *Cercospora personata*, *Botrytis cinerea*, species of *Alternaria*, *Verticillium alboatrum*, *Phialophora cinerescens* and species of *Fusarium*.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and bactericides, or insecticides, acaricides, nematocides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi and bacteria, and more particularly methods of combating fungi, which comprises applying to at least one of correspondingly (a) such fungi, (b) such bacteria, and (c) the corresponding habitat thereof, i.e. the locus to be protected, e.g. to a growing crop, to an area where a crop is to be grown or to a domestic animal, a correspondingly combative or toxic amount, i.e. a fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Pyricularia test; liquid preparation of active compound

Solvent: 1.9 parts by weight of DMF
Dispersing agent: 0.1 part by weight of alkylaryl polyglycol ether emulsifier
Water: 98 parts by weight The amount of active compound required for the desired concentration in the spray liquor was mixed with the stated amount of solvent, and the concentrate was diluted with the stated amount of water.

30 rice plants about 14 days old were sprayed with the spray liquor until dripping wet. The plants remained in a greenhouse at temperatures of 22° to 24°C and a relative atmospheric humidity of about 70% until they were dry. They were then inoculated with an aqueous suspension of 100,000 to 200,000 spores/ml of *Pyricularia oryzae* and placed in a chamber at 24°–26°C and 100% relative atmospheric humidity.

5 days after inoculation, the infection of all the leaves present at the time of inoculation was determined as a percentage of the untreated but also inoculated control plants. 0% means no infection: 100% means that the infection was exactly as great as in the case of the control plants.

The active compounds, the concentrations of the active compounds and the results can be seen from the following table:

Table 1

| *Pyricularia* test/liquid preparation of active compound | |  |
|---|---|---|
| Active compound | Infection in % of the infection of the untreated control at an active compound concentration (in %) of | |
| | 0.05 | 0.025 |
| $\begin{array}{c} \phantom{CH_2-NH-}S \\ \phantom{CH_2-NH-}\| \\ CH_2-NH-C-S \\ \phantom{CH_2-NH-CCCC}\diagdown \\ \phantom{CH_2-NH-CCCCCC}Zn \\ \phantom{CH_2-NH-CCCC}\diagup \\ CH_2-NH-C-S \\ \phantom{CH_2-NH-}\| \\ \phantom{CH_2-NH-}S \end{array}$ (A) (known) | 50 | |

Table 1-continued

| Active compound | Pyricularia test/liquid preparation of active compound Infection in % of the infection of the untreated control at an active compound concentration (in %) of | |
|---|---|---|
| | 0.05 | 0.025 |
| 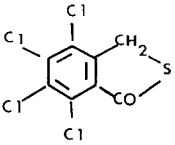 (I) | 0 | 0 |

EXAMPLE 2

Mycelium growth test

Nutrient medium used:

20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate Composition of solvent mixture:

0.19 part by weight of acetone
0.01 part by weight of alkylaryl polyglycol ether
1.80 parts by weight of water Proportion of solvent mixture to nutrient medium:

2 parts by weight of solvent mixture
100 parts by weight of agar nutrient medium The amount of active compound required for the desired concentration of active compound in the nutrient medium was mixed with the stated amount of solvent. The concentrate was thoroughly mixed, in the stated proportion, with the liquid nutrient medium, which had been cooled to 42°C, and was then poured into Petri dishes of 9 cm diameter. Control dishes to which the preparation had not been added were also set up.

When the nutrient medium had cooled and solidified, the dishes were inoculated with the species of fungi stated in the table and incubated at about 21°C.

Evaluation was carried out after 4–10 days, dependent upon the speed of growth of the fungi. When evaluation was carried out the radial growth of the mycelium on the treated nutrient media was compared with the growth on the control nutrient media. In the evaluation of the fungus growth, the following characteristic values were used:

```
    1 no fungus growth
up to 3 very strong inhibition of growth
up to 5 medium inhibition of growth
up to 7 slight inhibition of growth
    9 growth equal to that of untreated control.
```

The active compounds, their concentrations and the results obtained can be seen from the following table:

Table 2

| Active compound | Mycelium growth test Active compound concentration in ppm | *Pyricularia oryzae* | *Phytophthora cactorum* | *Pellicularia sasakii* |
|---|---|---|---|---|
| 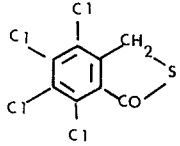 (I) | 100 | 5 | 5 | 5 |

(a)

EXAMPLE 3

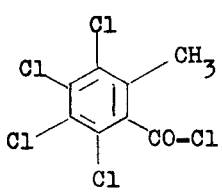

309 g (2 moles) of o-toluic acid chloride were chlorinated in the presence of 2 g of iron(III) chloride and 2 g of iodine in the temperature range between 20° and 60°C until a weight increase of 276 g was reached after 13 hours. The mixture was stirred with 250 ml of acetonitrile and the crystals which separated out were filtered off at 0°C and recrystallized from 500 ml of acetonitrile. 473 g (representing 81% of theory) of tetrachloro-o-toluic acid chloride were obtained as colorless crystals of melting point 70°C.

$C_8H_3Cl_5O$ (292.5): Calculated: C, 32.82; H, 1.03; Cl, 60.68; O, 5.47. Found: C, 32.5; H, 1.0; Cl, 60.9; O, 5.5.

(b)

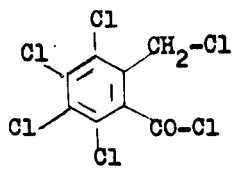

146.3 g (0.5 mole) of the product of (a) were chlorinated under exposure to a UV lamp (type Osram Hg H 2,000; 450 watt) at 90° to 110°C until a weight increase of 17.5 g was reached. The mixture was then stirred for a further hour at 90°C while exposed to the lamp. After cooling, the product was recrystallized from 200 ml of acetonitrile and dried in vacuo at 40°C. 134 g (representing 82% of theory) of 2-chloromethyl-3,4,5,6-tetrachlorobenzoyl chloride of melting point 77°–78°C were obtained.

$C_8H_2Cl_6O$ (327) Calculated: C, 29.36; H, 0.62; Cl, 64.14; O, 4.89. Found: C, 29.5; H, 0.7; Cl, 65.0; O, 5.1.

(c) 4,5,6,7-Tetrachloro-2-thio-phthalide

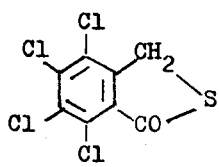 (I)

48 g (0.2 mole) of sodium sulfide containing water of crystallization ($Na_2S.9H_2O$) were dissolved in 300 ml of methanol. 6.8 g (0.2 mole) of hydrogen sulfide were passed into this solution at 10° to 20°C and 32.7 g (0.1 mole) of 2-chloromethyl-3,4,5,6-tetrachlorobenzoyl chloride were then introduced at 20° to 30°C. The mixture was boiled for 6 hours under reflux and after cooling to 10°C was acidified to pH 5 with concentrated hydrochloric acid. The crystal paste which separated out was filtered off, and the residue was washed with water and acetone and dried. The yield was 27.5 g (representing 95.5% of theory) of almost colorless crystalline powder of melting point 181°–183°C.

$C_8H_2Cl_4OS$ (288): Calculated: C, 33.33; H, 0.70; Cl, 49.31; O, 5.55; S, 11.11. Found: C, 33.3; H, 1.0; Cl, 49.1; O, 5.5; S, 11.0.

(d) Special purification process:

28.8 g (0.1 mole) of crude 4,5,6,7-tetrachloro-2-thiophthalide were dissolved in 200 ml of 10% strength sodium hydroxide solution and impurities were filtered off. The solution was acidified with acetic acid, whereupon colorless crystals of melting point 183°–184°C separated out. The yield was 24.0 g, representing 83% of theory.

It will be appreciated that the instant specification and examples are set forth by way of illustration and not limitation, and that various modifications and changes may be made without departing from the spirit and scope of the present invention.

What is claimed is:

1. 4,5,6,7-Tetrachloro-2-thio-phthalide of the formula

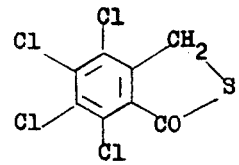

2. A process for the preparation of 4,5,6,7-tetrachloro-2-thio-phthalide according to claim 1, in which an alkali metal salt of 2-mercaptomethyl-3,4,5,6-tetrachloro-thiolbenzoic acid, of the formula

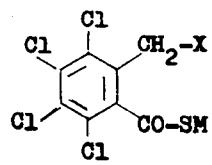

in which
  X is SH or SM, and
  M is an alkali metal,
is treated with an acid.

3. The process according to claim 2, in which M is sodium or potassium.

4. The process according to claim 2, in which the reaction is effected in the presence of a water-miscible, organic solvent.

5. The process according to claim 2, in which the reaction is effected between about −10° and 40°C.

6. A process according to claim 2, in which the acid is hydrochloric acid or sulfuric acid.

7. The process according to claim 2, in which the salt of 2-mercaptomethyl-3,4,5,6-tetrachlorothiolbenzoic acid is reacted in situ after having been prepared by the reaction of 2-chloromethyl-3,4,5,6-tetrachloro-benzoyl chloride with sodium hydrogen sulfide in alcoholic solution.

8. The process according to claim 6, in which M is sodium or potassium, the acid is added to produce a pH of about 5 to 6, and the reaction is effected between about 0° and 20°C.

* * * * *